(12) United States Patent
Choi et al.

(10) Patent No.: US 9,619,906 B2
(45) Date of Patent: Apr. 11, 2017

(54) X-RAY IMAGING APPARATUS AND CONTROL METHOD FOR THE SAME

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Jiyoung Choi, Suwon-si (KR); Young Hun Sung, Hwaseong-si (KR); Jae Hak Lee, Yongin-si (KR); Changhwan Kim, Daejeon (KR); Miran Park, Daejeon (KR); Seungryong Cho, Daejeon (KR)

(73) Assignees: SAMSUNG ELECTRONICS CO., LTD., Suwon-si (KR); KOREA ADVANCED INSTITUTE OF SCIENCE AND TECHNOLOGY, Daejeon-si (KR)

( * ) Notice: Subject to any disclaimer, the term of this patent is extended or adjusted under 35 U.S.C. 154(b) by 0 days.

(21) Appl. No.: 14/728,070

(22) Filed: Jun. 2, 2015

(65) Prior Publication Data
US 2015/0371414 A1    Dec. 24, 2015

(30) Foreign Application Priority Data
Jun. 20, 2014  (KR) .................. 10-2014-0075990

(51) Int. Cl.
*G06K 9/00* (2006.01)
*G06T 11/00* (2006.01)
(Continued)

(52) U.S. Cl.
CPC ............ *G06T 11/005* (2013.01); *G01N 23/04* (2013.01); *G06T 5/003* (2013.01); *G06T 2207/10116* (2013.01)

(58) Field of Classification Search
USPC ....... 382/100, 103, 106–107, 128, 132, 154, 382/162, 168, 173, 181, 199, 209, 232,
(Continued)

(56) References Cited

U.S. PATENT DOCUMENTS

2003/0072417 A1* 4/2003 Kaufhold ............... A61B 6/482
378/207
2004/0030246 A1* 2/2004 Townsend ............. A61B 6/032
600/427
(Continued)

*Primary Examiner* — Seyed Azarian
(74) *Attorney, Agent, or Firm* — Sughrue Mion, PLLC

(57) ABSTRACT

Disclosed herein are an X-ray imaging apparatus and a method for the same. The X-ray imaging apparatus includes a kernel function setter configured to set a scatter kernel function in response to a scatter component included in first X-ray image data detected by an X-ray detector, and an image data corrector configured to generate second X-ray image data obtained by performing scatter correction on the first X-ray image data using the scatter kernel function and data consistency. According to the X-ray imaging apparatus and the control method for the same, scatter correction is performed by using data consistency so that accuracy of the scatter correction may be increased and an X-ray image may be generated based on the accuracy, thereby improving quality of the X-ray image.

13 Claims, 15 Drawing Sheets

(51) Int. Cl.
*G01N 23/04* (2006.01)
*G06T 5/00* (2006.01)
*A61B 6/00* (2006.01)

(58) Field of Classification Search
USPC ....... 382/254, 274, 276, 280, 291, 305, 312, 382/131, 133; 378/4, 21, 207, 7; 600/427
See application file for complete search history.

(56) References Cited

U.S. PATENT DOCUMENTS

| | | | | |
|---|---|---|---|---|
| 2004/0264629 | A1* | 12/2004 | Tang | A61B 6/032 378/7 |
| 2008/0002807 | A1* | 1/2008 | Debasish | A61B 6/00 378/7 |
| 2010/0046696 | A1* | 2/2010 | Maltz | G06T 11/005 378/7 |

* cited by examiner (b)

(a)

X-RAY IMAGING APPARATUS AND CONTROL METHOD FOR THE SAME

CROSS-REFERENCE TO RELATED APPLICATION

This application claims priority from Korean Patent Application No. 10-2014-0075990, filed on Jun. 20, 2014 in the Korean Intellectual Property Office, the disclosure of which is incorporated herein by reference in its entirety.

BACKGROUND

1. Field

Exemplary embodiments relate to an X-ray imaging apparatus and control method for the same.

2. Description of the Related Art

An X-ray imaging apparatus is an apparatus that can radiate X-rays toward an object such as a human body or an object and acquire an internal image of the object using the X-rays which propagate through the object. Transmissivity of the X-rays varies according to characteristics of a material of which the object is constituted, and therefore the internal structure of the object can be visualized by detecting the intensity or strength of the X-rays which propagate through the object. The internal structure of the object may be readily determined by using the X-ray imaging apparatus, and therefore the X-ray imaging apparatus may be used in detecting disorders such as lesions of a human body in the medical field or in checking the inside of baggage in an airport.

Examples of such an X-ray imaging apparatus include a digital radiography (DR) apparatus, a computed tomography (CT) apparatus, a full field digital mammography (FFDM) apparatus, and the like.

The X-ray imaging apparatus includes an X-ray source that radiates X-rays and an X-ray detector that detects X-rays which propagate through an object, and an X-ray image is generated based on data output from the X-ray detector. In order to generate the X-ray image close to an ideal image inside the object, techniques have been developed through hardware by changing the structure of the X-ray imaging apparatus and through software by applying changes to a variety of computation, correction, or restoration methods.

SUMMARY

Therefore, it is an aspect of one or more exemplary embodiments to provide an X-ray imaging apparatus that performs scatter correction and a control method for the same.

Additional aspects of the exemplary embodiments will be set forth in part in the description which follows and, in part, will be obvious from the description, or may be learned by practice of the exemplary embodiments.

In accordance with one aspect of one or more exemplary embodiments, an X-ray imaging apparatus includes: a kernel function setter configured to set a scatter kernel function in response to a scatter component included in first X-ray image data detected by an X-ray detector; and an image data corrector configured to generate second X-ray image data obtained by performing scatter correction on the first X-ray image data by using the scatter kernel function and a data consistency.

Here, the image data corrector may be further configured to generate corrected image data obtained by performing scatter correction on the first X-ray image data by using the scatter kernel function.

Also, the image data corrector may be further configured to generate the corrected image data by performing a deconvolution on the first X-ray image data and the scatter kernel function.

Also, the image data corrector may be further configured to perform the deconvolution on the first X-ray image data and the scatter kernel function by using the following Equation 4:

$$I_{qi} = F^{-1}\left(\frac{F(I_m)}{F(\delta + K_i)}\right) \quad \text{[Equation 4]}$$

where $I_{qi}$ denotes corrected image data, $I_m$ denotes first X-ray image data, $\delta$ denotes a delta function, $K_i$ denotes a scatter kernel function, F denotes a Fourier transform, and $F^{-1}$ denotes an inverse Fourier transform.

Also, the X-ray imaging apparatus may further include a data consistency determiner configured to determine whether the corrected image data satisfies the data consistency.

Also, the data consistency determiner may be further configured to convert the corrected image data into parallel-beam type corrected image data by performing fan-parallel rebinning.

Also, the second X-ray image data may satisfy the data consistency.

Also, the kernel function setter may be further configured to update the scatter kernel function when the corrected image data is determined as not satisfying the data consistency.

Also, the kernel function setter may be further configured to set or update the scatter kernel function using the following Equation 3:

$$K_i(I_p, I_0, r) = A_i\left(\frac{I_p}{I_0}\right)^{\alpha_i} \cdot \left(\ln\left(\frac{I_0}{I_p}\right)\right)^{\beta_i} \cdot \left[\exp\left(\frac{-r^2}{2\sigma_i^2}\right) + B_i\exp\left(\frac{-r^2}{2\tau_i^2}\right)\right] \quad \text{[Equation 3]}$$

where $i \in N$, N denotes a natural number, each of $A_i$, $B_i$, $\alpha_i$, $\beta_i$, $\sigma_i$, and $\tau_i$ denotes a respective parameter, $I_p$ denotes a primary component included in the first X-ray image data, $I_0$ denotes an X-ray detected without an attenuation phenomenon when there is no object, r denotes a position on an X-ray detector at which each of $I_p$ and $I_0$ is detected, and $K_i(I_p, I_0, r)$ denotes an i-th scatter kernel function.

Also, the X-ray imaging apparatus may further include a display configured to display an X-ray image which corresponds to the second X-ray image data.

In accordance with another aspect of one or more exemplary embodiments, a control method which is executable by an X-ray imaging apparatus includes: setting a scatter kernel function in response to a scatter component included in first X-ray image data detected by an X-ray detector; and generating second X-ray image data obtained by performing scatter correction on the first X-ray image data by using the scatter kernel function and a data consistency.

Here, the generating the second X-ray image data may include generating corrected image data obtained by performing scatter correction on the first X-ray image data by using the scatter kernel function.

Also, the generating the second X-ray image data may include generating the corrected image data by performing a deconvolution on the first X-ray image data and the scatter kernel function.

Also, the generating of the second X-ray image data may include performing the deconvolution on the first X-ray image data and the scatter kernel function using the following Equation 4:

$$I_{qi} = F^{-1}\left(\frac{F(I_m)}{F(\delta + K_i)}\right) \quad \text{[Equation 4]}$$

where $I_{qi}$ denotes corrected image data, $I_m$ denotes first X-ray image data, $\delta$ denotes a delta function, $K_i$ denotes a scatter kernel function, F denotes a Fourier transform, and $F^{-1}$ denotes an inverse Fourier transform.

Also, the control method may further include determining whether the corrected image data satisfies the data consistency.

Also, the determining may include converting the corrected image data into parallel-beam type corrected image data by performing fan-parallel rebinning.

Also, the second X-ray image data may satisfy the data consistency.

Also, the setting the scatter kernel function may include updating the scatter kernel function when the corrected image data is determined as not satisfying the data consistency.

Also, the setting the scatter kernel function may include setting or updating the scatter kernel function using the following Equation 3:

$$K_i(I_p, I_0, r) = A_i\left(\frac{I_p}{I_0}\right)^{\alpha_i} \cdot \left(\ln\left(\frac{I_0}{I_p}\right)\right)^{\beta_i} \cdot \left[\exp\left(\frac{-r^2}{2\sigma_i^2}\right) + B_i\exp\left(\frac{-r^2}{2\tau_i^2}\right)\right] \quad \text{[Equation 3]}$$

where $i \in N$, N denotes a natural number, each of $A_i$, $B_i$, $\alpha_i$, $\beta_i$, $\sigma_i$, and $\tau_i$ denotes a respective parameter, $I_p$ denotes a primary component included in the first X-ray image data, $I_0$ denotes an X-ray detected without an attenuation phenomenon when there is no object, r denotes a position on an X-ray detector at which each of $I_p$ and $I_0$ is detected, and $K_i(I_p, I_0, r)$ denotes an i-th scatter kernel function.

Also, the control method may further include displaying an X-ray image which corresponds to the second X-ray image data.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
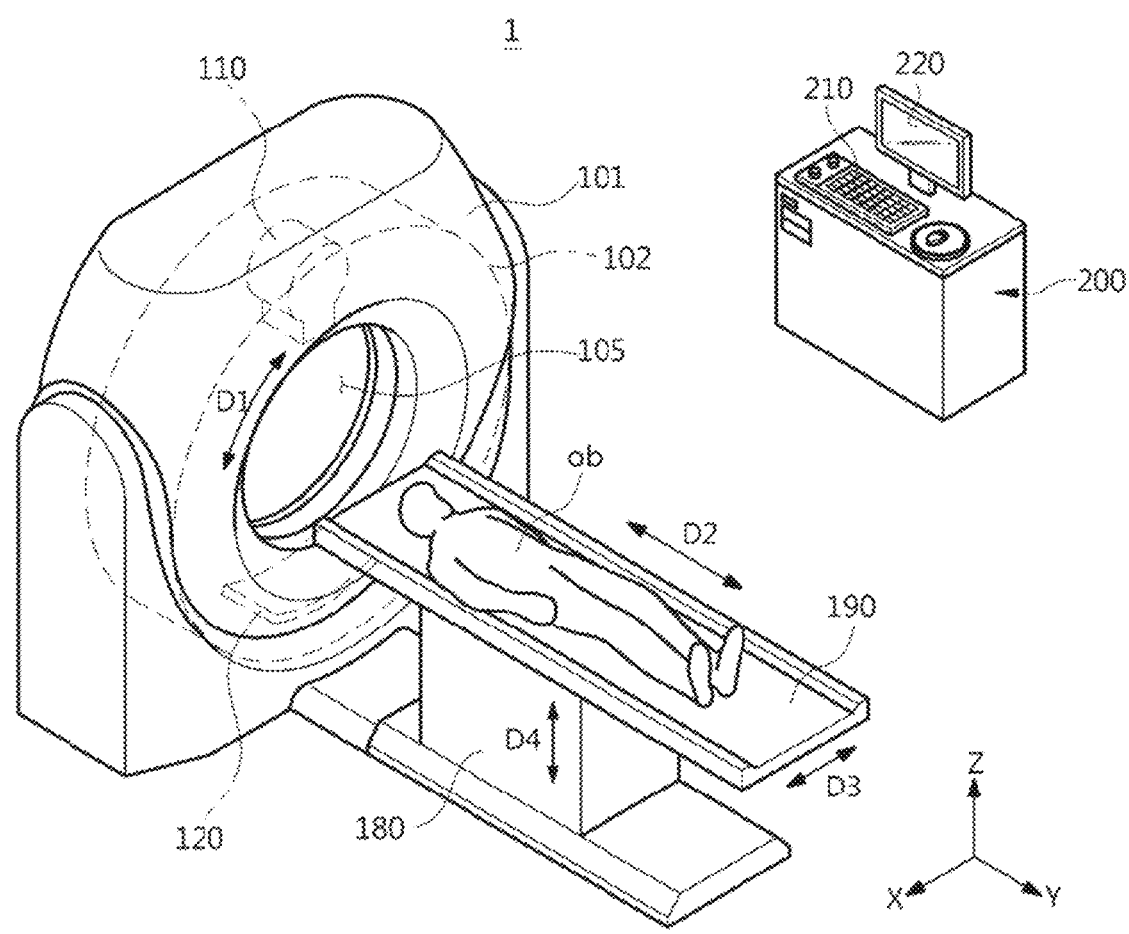
FIG. 1 is a perspective diagram showing the appearance of an X-ray imaging apparatus, in accordance with one exemplary embodiment.

Exemplary embodiments described in the present specification and configurations shown in drawings are merely preferable examples for the purpose of illustration only, not intended to limit the scope of the present disclosure, and thus it should be understood that other equivalents and modifications could be made thereto without departing from the spirit and scope of the present disclosure.

Hereinafter, an X-ray imaging apparatus and a control method for the X-ray imaging apparatus will be described in detail in accordance with exemplary embodiments which will be described with reference to the accompanying drawings. Like reference numerals refer to like elements throughout.

The structure or radiography method of the X-ray imaging apparatus may be changed depending on a radiographic part, the kind of an X-ray image, and/or the purpose of radiography. Specifically, there are a general X-ray imaging apparatus that performs radiography on the chest, arms, legs, etc., an X-ray imaging apparatus that uses mammography, an X-ray imaging apparatus that uses fluoroscopy, an X-ray imaging apparatus that uses angiography, an X-ray imaging apparatus for cardiography, an X-ray imaging apparatus that uses tomography, and the like, and the X-ray imaging apparatus according to an exemplary embodiment may include one of the above-described X-ray imaging apparatuses and/or a combination of at least two thereof.

Hereinafter, for convenience of description, the X-ray imaging apparatus that uses tomography, and in particular, an X-ray imaging apparatus that is implemented as a computed tomography (CT) apparatus, will be described.

FIG. 1 is a perspective diagram showing the appearance of an X-ray imaging apparatus, in accordance with one exemplary embodiment.

As shown in FIG. 1, the X-ray imaging apparatus 1 may include a housing 101 configured for radiating and detecting X-rays, a table 190 configured for moving an object (ob), and a main body 200 configured for controlling operations of the X-ray imaging apparatus 1.

A cylindrical gantry 102 is mounted inside the housing 101. Inside the gantry 102, an X-ray source 110 that radiates X-rays and an X-ray detector 120 that detects X-rays are provided so as to face each other. The X-ray source 110 generates X-rays and irradiates the object (ob) with the generated X-rays, and includes a filtering unit (also referred to herein as a "filter") that filters the radiated X-rays to be provided in the form of an X-ray source assembly. Here, the object (ob) is not limited, provided that the internal structure of the object (ob) can be visualized by the X-ray imaging apparatus 1, such as a human, an animal, an object, and the like.

The X-ray detector 120 may detect the X-rays which propagate through the object (ob), and may be provided on an opposite side of the X-ray source 110. The object (ob) may be positioned between the X-ray source 110 and the X-ray source 110 according to the movement of the table 190, and the X-rays radiated from the X-ray source 110 may propagate through the object to be detected by the X-ray detector 120.

The gantry 102 may be rotated around a bore 105 at a constant angular velocity in accordance with a driving command, and therefore the X-ray source 110 and the X-ray detector 120 provided in the gantry 102 are also rotated while forming a predetermined axis. In this instance, the rotation direction of the gantry 102 may be defined as a direction D1. Detailed descriptions of the rotation of the gantry 102 will be provided below with reference to FIG. 2.

Figure 2:
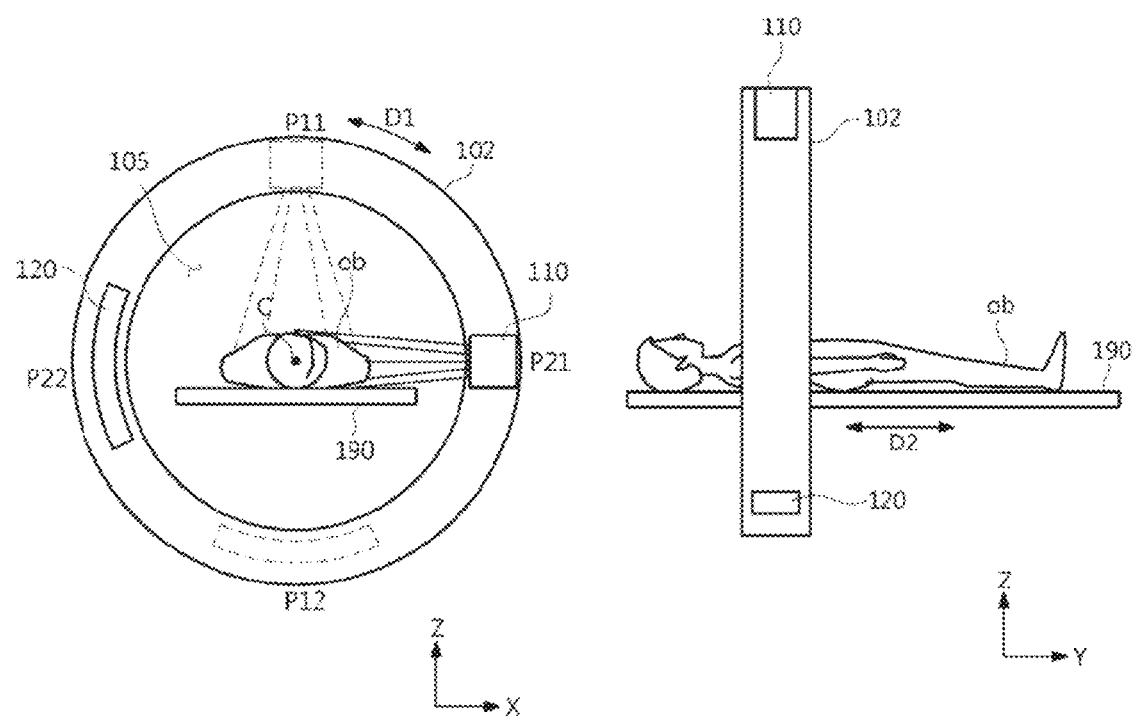
FIG. 2 illustrates rotation of a gantry and movement of a table.

FIG. 2 illustrates rotation of a gantry and movement of a table.

As shown on the left in FIG. 2, the gantry 102 may start rotation in a direction D1 when X-ray radiography begins. The gantry 102 is rotated in accordance with a rotation rate and rotation speed which are input by a user or determined in advance, and the X-ray source 110 radiates X-rays toward the object (ob) at a predetermined period or time interval. The X-ray detector 120 detects the X-rays which propagate through the object (ob) while rotating together with the X-ray source 110. For example, the X-ray source 110 rotates 360° using a position P11 as a starting position, passes through a position P21, and returns to the position P11, and radiates X-rays multiple times while rotating. The X-ray detector 120 rotates 360° using a position P12 as a starting position to correspond to the position of the X-ray source 110, passes through a position P22, and returns to the position P12. While returning to the position P12, the X-ray detector 120 converts received X-rays which correspond to each instance of X-ray radiation into electrical signals in order to detect the electrical signals. The X-rays detected in this manner may be defined as first X-ray image data.

The table 190 may be moved in directions of an X axis, a Y axis, and a Z axis while remaining level with the ground. In this instance, a direction of the Y axis in which the table 190 is moved may be defined as a direction D2, a direction of the X axis in which the table 190 is moved may be defined as a direction D3, and a direction of the Z axis in which the table 190 is moved may be defined as a direction D4.

The table 190 transports the object (ob) that is a target of the X-ray radiography into a bore 105 as shown on the right in FIG. 2. The horizontal position or vertical height of the table 190 is adjusted while the table 190 is moved in the direction D3 or D4 and then moved into the bore 105. Alternatively, the table 190 may be moved into the bore 105 and then moved in the direction D3 or D4, so that the horizontal position or vertical height of the table 190 can be adjusted.

When the center of the object (ob) deviates from the center (C) of the bore 105, the table 190 is moved in the direction D3 or D4 by a distance from the center (C) to align the center of the object (ob) with the center (C) of the bore 105. Thus, the X-ray imaging apparatus 1 may acquire a clearer X-ray image.

The table 190 may enable a desired diagnostic region on which radiography is performed to be positioned between the X-ray source 110 and the X-ray detector 120 while being moved in the directions D2, D3, and D4. The diagnostic region may be the whole object (ob), or include only a partial region inside the object (ob). The diagnostic region may include a region of interest (ROI).

Figure 5:
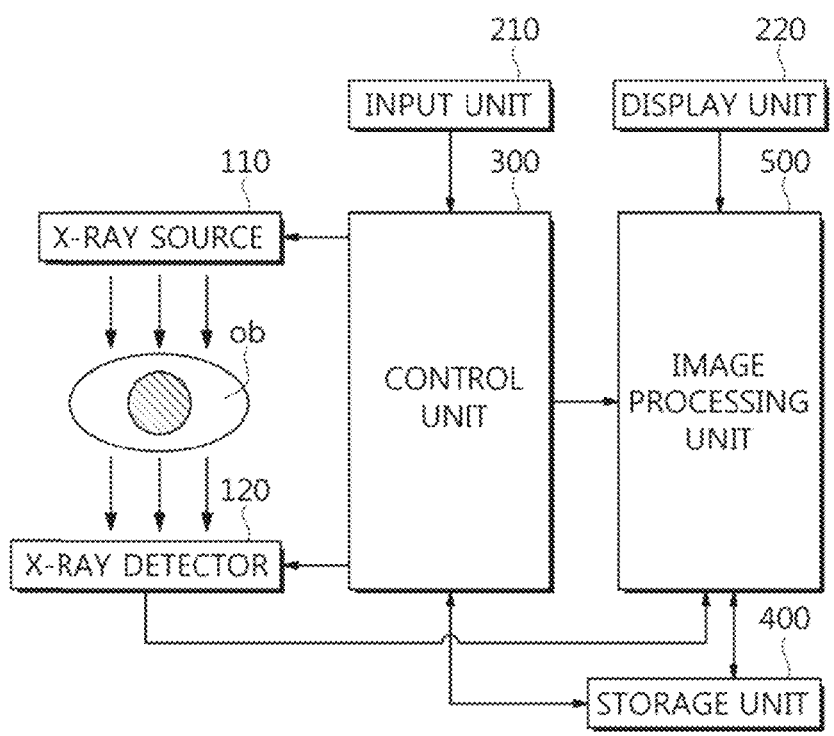
FIG. 5 is a control block diagram showing an X-ray imaging apparatus, in accordance with one exemplary embodiment.

The main body 200 may receive main components of the X-ray imaging apparatus 1, for example, a control unit (also referred to herein as a "controller") (see 300 of FIG. 5). The control unit 300 may generate any one or more of a variety of control signals for operations of the X-ray imaging apparatus 1, such as, for example, controlling rotation of the gantry 102 or movement of the table 190, or controlling the dose of the X-rays radiated from the X-ray source 110, and this will be described in detail below.

A user interface for user operation may be provided on an upper portion of the main body 200. The user interface may include an input unit (also referred to herein as an "input device") 210 that receives a user command for manipulating operations of the X-ray imaging apparatus 1, and a display unit (also referred to herein as a "display" and/or as a "display device") 220 that provides various screens related to the operations of the X-ray imaging apparatus 1. Here, a user may be a person who performs diagnosis of an object by using the X-ray imaging apparatus 1, that is, a medical staff including a doctor, a radiologist, a nurse, and the like, but is not limited thereto. The user is not limited provided that the user can use the X-ray imaging apparatus 1.

The input unit 210 may include a hardware input device such as any one or more of various buttons and switches, a keyboard, a mouse, a track-ball, various levers, a handle, a stick, and the like for the purpose of the user's input. The input unit 210 may be provided on an upper portion of the main body 200 as shown in FIG. 1, or provided on a lower portion thereof when the input unit 210 is implemented by a foot switch, a foot pedal, and the like.

The input unit 210 may include a graphical user interface (GUI) such as a touch pad for the user's input, that is, a software input device. The touch pad may be implemented by a touch screen panel (TSP) to form a mutual layer structure with the display unit 220 which will be described below.

The user may input an X-ray radiography start command, a movement command of the table 190, and the like via the input unit 210, and select the kind of radiography or set a diagnostic region. The user command input via the input unit 210 may be transmitted to the main body 200 through wired or wireless communication.

The display unit 220 may be provided as any one or more of a cathode ray tube (CRT), a digital light processing (DLP) panel, a plasma display panel, a liquid crystal display (LCD) panel, an electroluminescence (EL) panel, an electrophoretic display (EPD) panel, an electrochromic display (ECD) panel, a light emitting diode (LED) panel, an organic light emitting diode (OLED) panel, or the like, but is not limited thereto.

As described above, when the display unit 220 is constituted of a TSP that forms the mutual layer structure with the touch pad, the display unit 132 may be used not only as a display device, but also as an input device.

The display unit 220 may display a screen related to operation information of the X-ray imaging apparatus 1, such as, for example, any one or more of a screen for selecting the kind of radiography, a screen for setting a field of view (FOV), or the like, and display X-ray images acquired by X-ray radiography. Here, the X-ray image is the same image as an ideal image inside the object or close to the ideal image and is generated by performing correction or the like on the first X-ray image data of the X-ray detector 120, and generation of the X-ray images will be described specifically below.

The X-ray image acquired by X-ray radiography may include any one or more of a single cross-sectional image, a plurality of cross-sectional images, or a three-dimensional (3D) image or a 3D stereo image generated based on the plurality of cross-sectional images in accordance with the kind of X-ray radiography. In this instance, the 3D image refers to an image obtained by performing volume rendering on 3D volume data generated based on the plurality of cross-sectional images on the basis of a predetermined point of sight. In particular, the 3D image denotes a 2D projected image obtained by projecting volume data to a 2D plane on the basis of a predetermined point of sight. The 3D stereo image refers to an image obtained in such a manner that left and right images are obtained by performing volume rendering on volume data at two points of sight corresponding to left and right eyes of a human body and the two obtained images are combined.

The display unit 220 may include a plurality of display devices as shown in FIG. 1, and display different kinds of screens. As an example, the display unit 220 may include a first display device and a second display device. Here, a single cross-sectional image may be displayed on the first display device, and a 3D image or a 3D stereo image may be displayed on the second display device. As another example, a screen related to operation information of the X-ray imaging apparatus 1 may be displayed on the first display device, and X-ray images acquired by X-ray radiography may be displayed on the second display device.

The X-ray imaging apparatus (1, hereinafter referred to as a "gantry type X-ray imaging apparatus") in which the housing 101 and the gantry 102 are provided has been described above, but the X-ray imaging apparatus 1 may have a structure which is different from that of FIG. 1.

Figure 3:
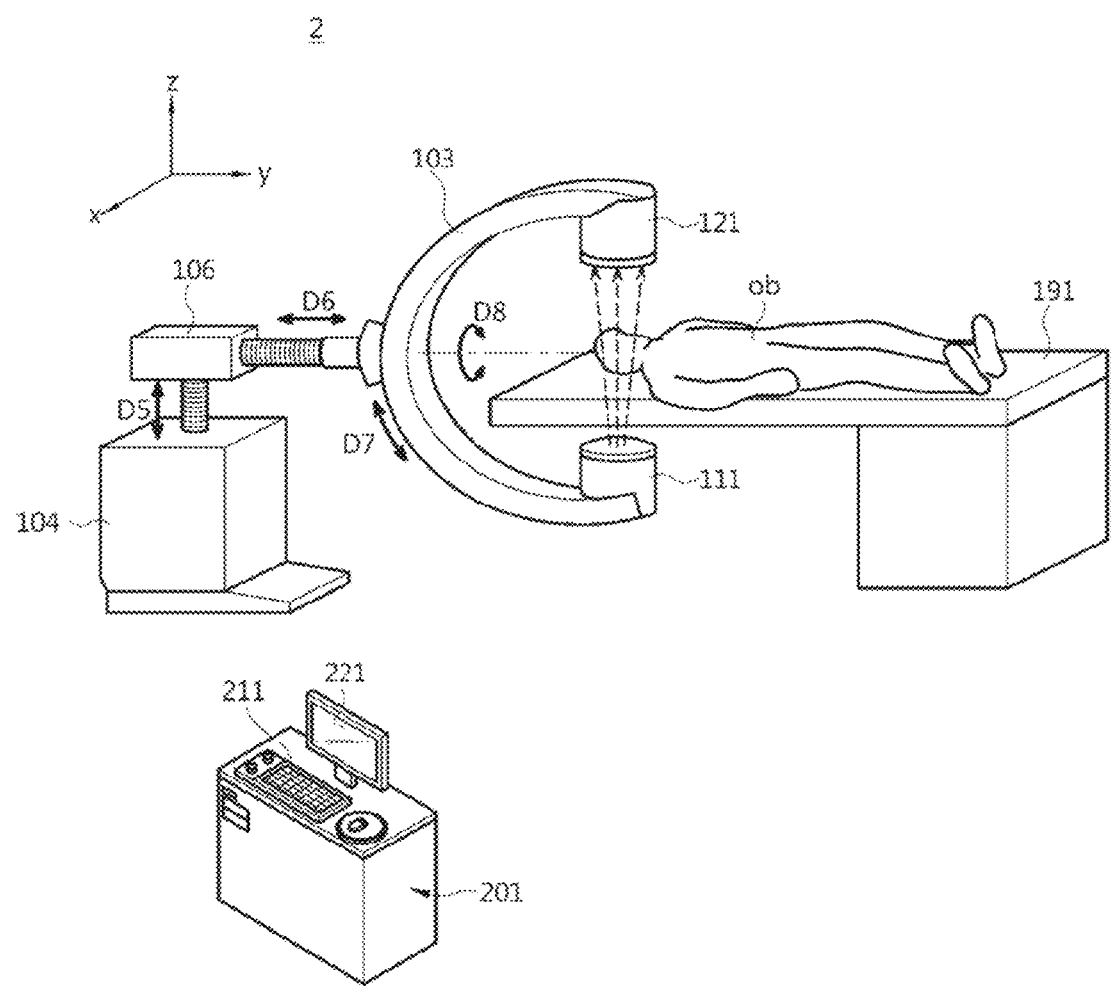
FIG. 3 illustrates the appearance an X-ray imaging apparatus, in accordance with another exemplary embodiment.

FIG. 3 illustrates the appearance an X-ray imaging apparatus, in accordance with another exemplary embodiment.

The X-ray imaging apparatus 2 may have a C-shaped arm (C-arm 103) structure as shown in FIG. 3. An X-ray source 110 that radiates X-rays and an X-ray detector 121 that detects X-rays may be provided at both ends of the C-arm 103 so that the X-ray source 110 and the X-ray detector 121 face each other. As described above, the X-ray source 110 may include a filtering unit that filters radiated X-rays to be provided in the form of an X-ray source assembly.

The C-arm 103 may be connected to a support unit (also referred to herein as a "support" and/or as a "support structure") 104 through a connection shaft 106, and moved in directions of the Y axis and the Z axis in accordance with movement of the connection shaft 106. In this instance, a direction in which the C-arm 103 is moved in the direction of the Z axis may be defined as a direction D5, and a direction in which the C-arm 102 is moved in the direction of the Y axis may be defined as a direction D6. The C-arm 103 may enable a desired diagnostic region on which radiography is performed to be positioned between the X-ray source 110 and the X-ray detector 120 while rotating in the directions D5 and D6.

In addition, the C-arm 103 may be provided so as to be rotated in an orbital direction and rotated in a lateral direction D4 using the direction D6 as a reference axis. In this instance, a direction in which the C-arm 103 is rotated in the orbital direction may be defined as a direction D7, and a direction in which the C-arm is rotated with respect to the direction D6 may be defined as a direction D8. The C-arm 103 is rotated in the direction D7 or D8, and therefore the X-ray source 110 and the X-ray detector 121 positioned at both ends of the C-arm 103 may also be rotated.

Figure 4A:
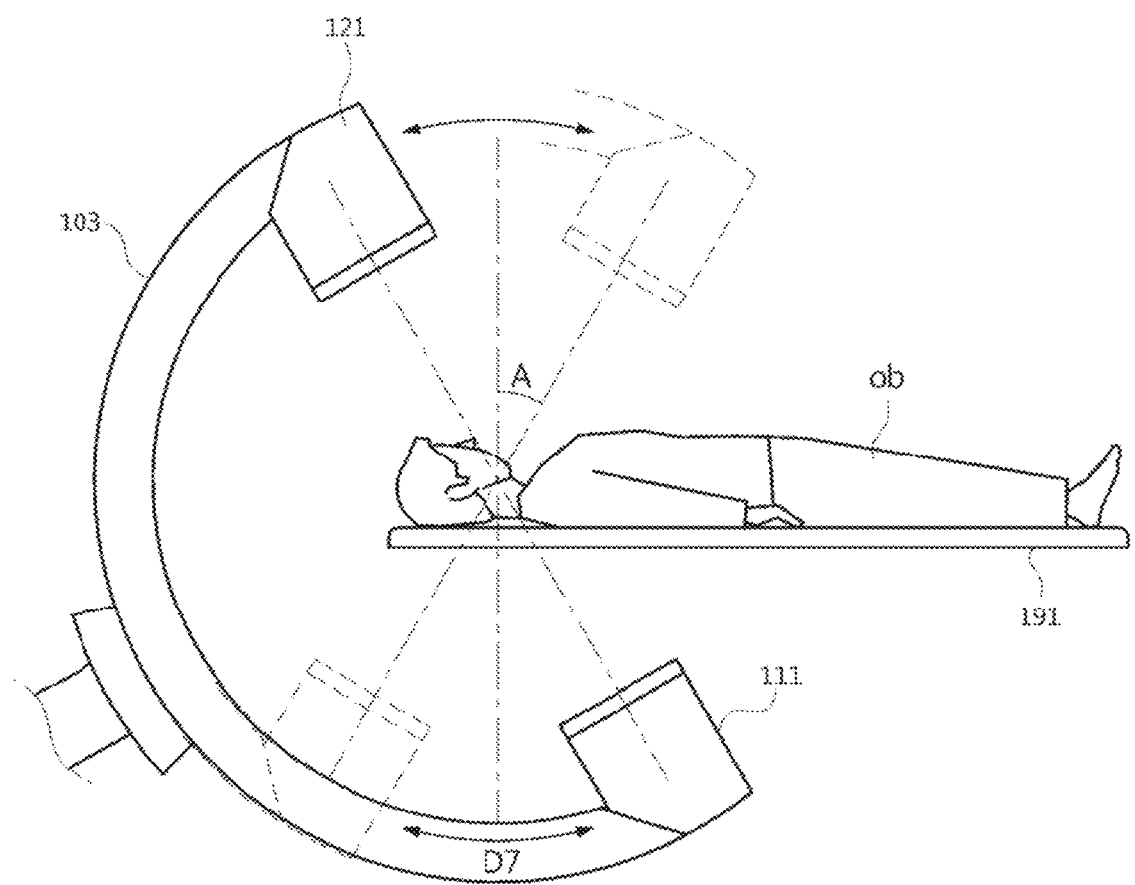
FIG. 4A illustrates a C-arm that is rotated in a first direction.
Figure 4B:
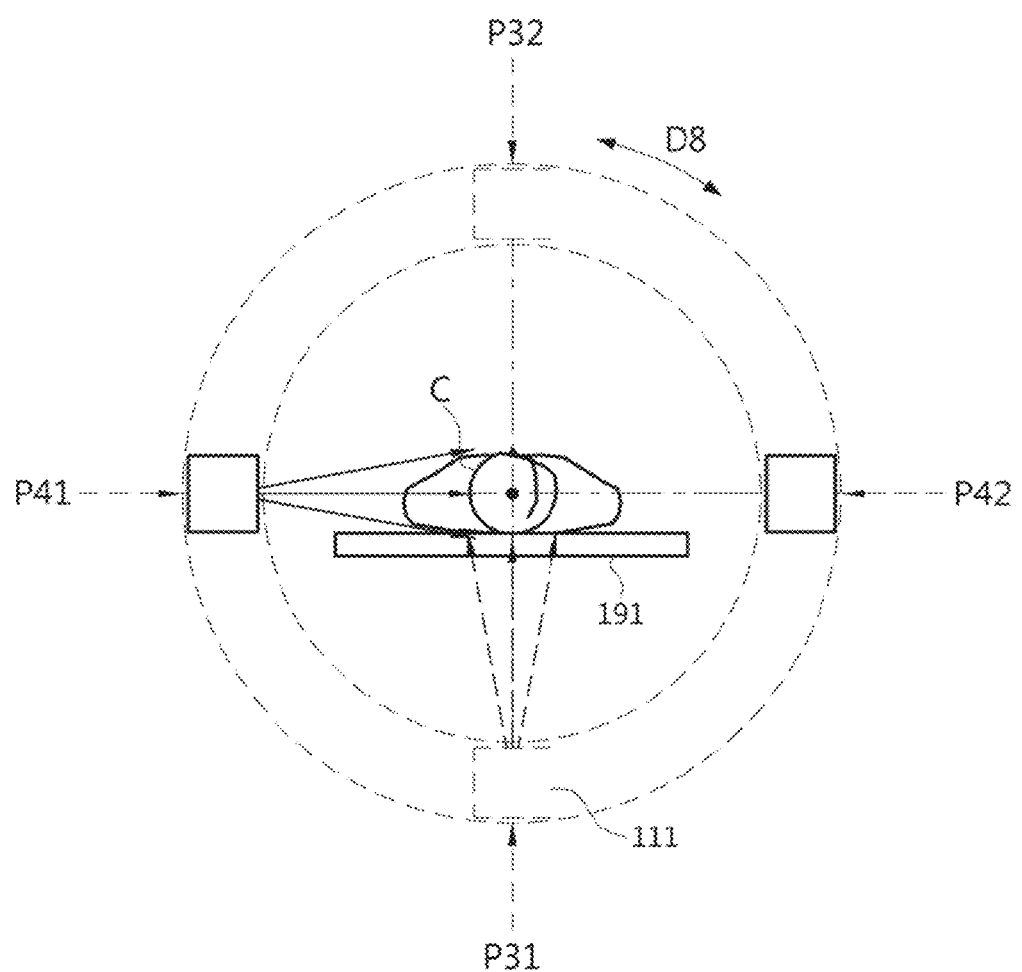
FIG. 4B illustrates a C-arm that is rotated in a second direction.

FIG. 4A illustrates the C-arm being rotated in a direction D7, and FIG. 4B illustrates the C-arm being rotated in a direction D8.

First, the C-arm 103 may be rotated in the direction D7 by a predetermined angle. For example, as shown in FIG. 4A, the C-arm may be rotated in one direction by an angle A, in the opposite direction by an angle 2A, or in one direction by the angle 2A. The C-arm 103 may be rotated 360° in the direction D8. Thus, as shown in FIG. 4B, the X-ray source 110 mounted at one end of the C-arm 103 starts to be rotated, passes through a position P41, and returns to a position P31, and therefore the X-ray detector 121 may pass through a position P42 starting from a position P32, and return to the position P32.

The table 191 may be a portion for seating the object (ob), and moved in directions of the X axis, the Y axis, and the Z axis while remaining level to the ground. A diagnostic region of the object (ob) may be positioned between the X-ray source 110 and the X-ray detector 120 in accordance with the movement of the table 191 even when the C-arm is not moved.

A C-arm type X-ray imaging apparatus 2 may include a main body 201 and a user interface provided in the main body 201, that is, an input unit 211 and a display unit 221 in the same manner as in the gantry type X-ray imaging apparatus 1, and the main body 201 and the user interface are the same as in FIG. 1.

The X-ray imaging apparatus may be provided in the form of a gantry as shown in FIG. 1 or provided in the form of C-arm, but for convenience of description, a case in which the X-ray imaging apparatus is the gantry type X-ray imaging apparatus 1 will be described herein.

FIG. 5 is a control block diagram showing an X-ray imaging apparatus, in accordance with one exemplary embodiment.

Referring to FIG. 5, the X-ray imaging apparatus 1 may include an input unit (also referred to herein as an "input device") 210, an X-ray detector 120, a control unit (also referred to herein as a "controller") 300, a storage unit (also referred to herein as a "storage device" and/or as a "storage") 400, an image processing unit (also referred to herein as an "image processor") 500, and a display unit (also referred to herein as a "display device" and/or as a "display") 220, and may generate and display X-ray images.

Figure 6:
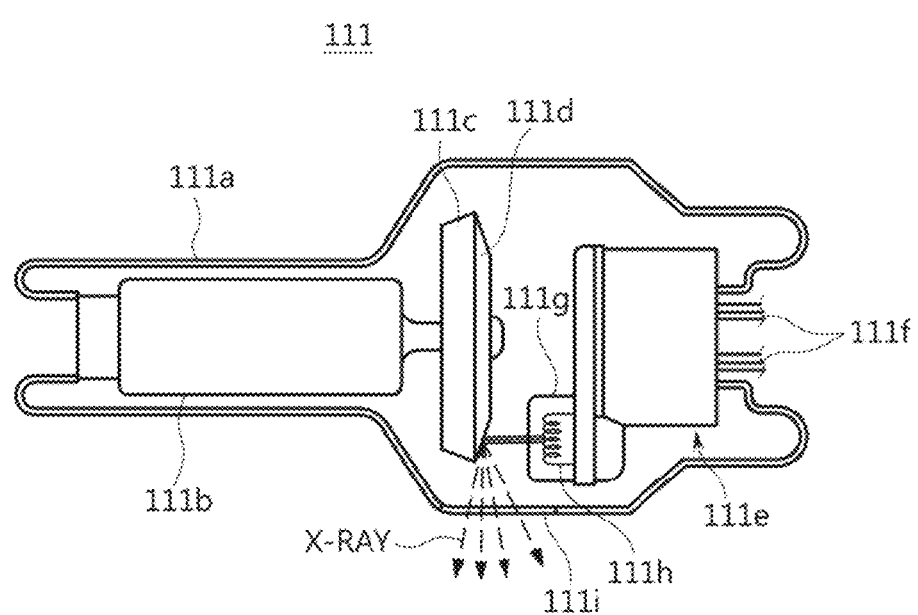
FIG. 6 is a cross-sectional diagram illustrating an internal structure of an X-ray tube.

The X-ray source 110 is a device that generates X-rays in order to irradiate an object (ob) with the generated X-rays, and may include an X-ray tube 111 for generating X-rays as shown in FIG. 6. FIG. 6 is a cross-sectional diagram illustrating an internal structure of an X-ray tube.

The X-ray tube 111 may be implemented by a diode vacuum tube which includes an anode 111c and a cathode 111e, and the tubular body may be implemented as a glass tube 111a made of a rigid silicate glass or the like.

The cathode 111e includes a focusing electrode 111g that focuses filaments 111h and electrons, and the focusing electrode 111g may be referred to as a focusing cup. Thermoelectrons are generated in such a manner that the inside of the glass tube 111a is in a high vacuum state of approximately 10 mmHg and the filaments 111h of the cathode are heated to a high temperature. As an example of the filaments 111h, tungsten filaments may be used, and the filaments 111h may be heated by applying a current to an electric lead wire 111f connected to the filaments 111h. However, the disclosed exemplary embodiment is not limited to adopting the filaments 111h in the cathode 111e, and a carbon nano-tube that can be driven by a high-speed pulse may be used as the cathode 111e.

The anode 111c may be primarily made of copper, and a target material 111d may be coated or disposed on a side of the cathode 111e that faces the cathode 111e. As the target material, high-resistance materials such as any one or more of Cr, Fe, Co, Ni, W, Mo, and the like may be used. A focal spot size is reduced along with an increase in the melting point of the target material.

When a high voltage is applied between the cathode 111e and the anode 111c, the thermoelectrons are accelerated and collide with the target material 111d of the anode in order to generate X-rays. The generated X-rays are radiated to the outside through a window 111i, and a beryllium (Be) thin film may be used as a material of the window.

The target material 111d may be rotated by a rotor 111b, and when the target material 111d is rotated, a heat accumulation rate may be increased 10 times or more per unit area compared to a case in which the target material 111d is fixed, and the focal spot size may be reduced.

The voltage applied between the cathode 111e and the anode 111c of the X-ray tube 111 is referred to as a tube voltage, and the size of the tube voltage may be represented as a crest value kvp. When the tube voltage is increased, the speed of the thermoelectrons is increased and the thermoelectrons collide with the target material in order to generate X-rays, and therefore energy (energy of photons) of the generated X-rays is increased. A current flowing in the X-ray tube 111 may be referred to as a tube current, and represented as a mean value mA. When the tube current is increased, the dose of the X-rays (the number of photons of X-rays) is increased. In this aspect, the energy of the X-rays may be controlled by the tube voltage, and the dose of the X-rays may be controlled by the tube current and an X-ray exposure time.

The X-ray detector 120 is a device for detecting X-rays which are radiated from the X-ray source 110 and which propagate through the object (ob) or are directly transferred without propagating through the object (ob). The X-ray detector 120 may convert the transmitted or transferred X-rays into electrical signals to detect the electrical signals. In particular, the X-ray detector 120 may acquire first X-ray image data converted into the electrical signals, and the first X-ray image data acquired by the X-ray detector 120 may be transferred to the storage unit 400 or the image processing unit 500.

The X-ray detector 120 may be classified in accordance with a material of which the X-ray detector 120 is constituted, or according to whether a method of converting the detected X-rays into electrical signals or a method of acquiring electrical signals is used.

First, the X-ray detector 120 is classified as being constituted of a single element or constituted of a mixed element, in accordance with the material of which it is constituted.

A case in which the X-ray detector 120 is constituted of the single element corresponds to a case in which a portion that detects X-rays to generate electrical signals and a portion that reads and processes electrical signals are constituted of a semiconductor composed of a single material or manufactured in a single process, and for example, corresponds to a case in which single light-receiving element such as a charge coupled device (CCD) or a complementary metal oxide semiconductor (CMOS) is used.

A case in which the X-ray detector 120 is constituted of the mixed element corresponds to a case in which the portion that detects X-rays to generate electrical signals and the portion that reads and processes electrical signals are constituted of different materials or manufactured in different processes. For example, there are cases in which the X-rays are detected by using a light receiving element such as a photodiode, a CCD, or CdZnTe, and the electrical signals are read and processed using a CMOS read out integrated circuit (ROIC), cases in which the X-rays are detected by using a strip detector and the electrical signals are read and processed using the CMOS ROIC, cases in which an a-Si or a-Se flat panel system is used, and the like.

In addition, the method in which the X-ray detector 120 converts the X-rays into electrical signals is classified as a direct conversion method or an indirect conversion method.

In the direct conversion method, when X-rays are radiated, electron-hole pairs are temporarily generated inside a light receiving element, and the electrons move to the anode and the holes move to the cathode due to the electric field applied to both ends of the light receiving element. Here, the X-ray detector 120 converts such movement into electrical signals. In the direct conversion method, a-Se, CdZnTe, $HgI_2$, $PbI_2$, or the like may be used as a material of the light receiving element.

In the indirect conversion method, when X-rays radiated from the X-ray source 110 react with a scintillator to emit photons having wavelengths of the visible light region, the light receiving element detects the emitted photons and converts the detected photons into electrical signals. In the indirect conversion method, a-Si or the like may be used as the light receiving element, and a thin-film GADOX scintillator, a CSI (T1) having a micro columnar or needle structure, or the like may be used as the scintillator.

In addition, the method in which the X-ray detector 120 acquires electrical signals is classified as a charge integration mode of storing charges for a certain time and then acquiring signals from the stored charge, or a photon counting mode of performing counting every time signals are generated by a single X-ray photon.

Figure 7:
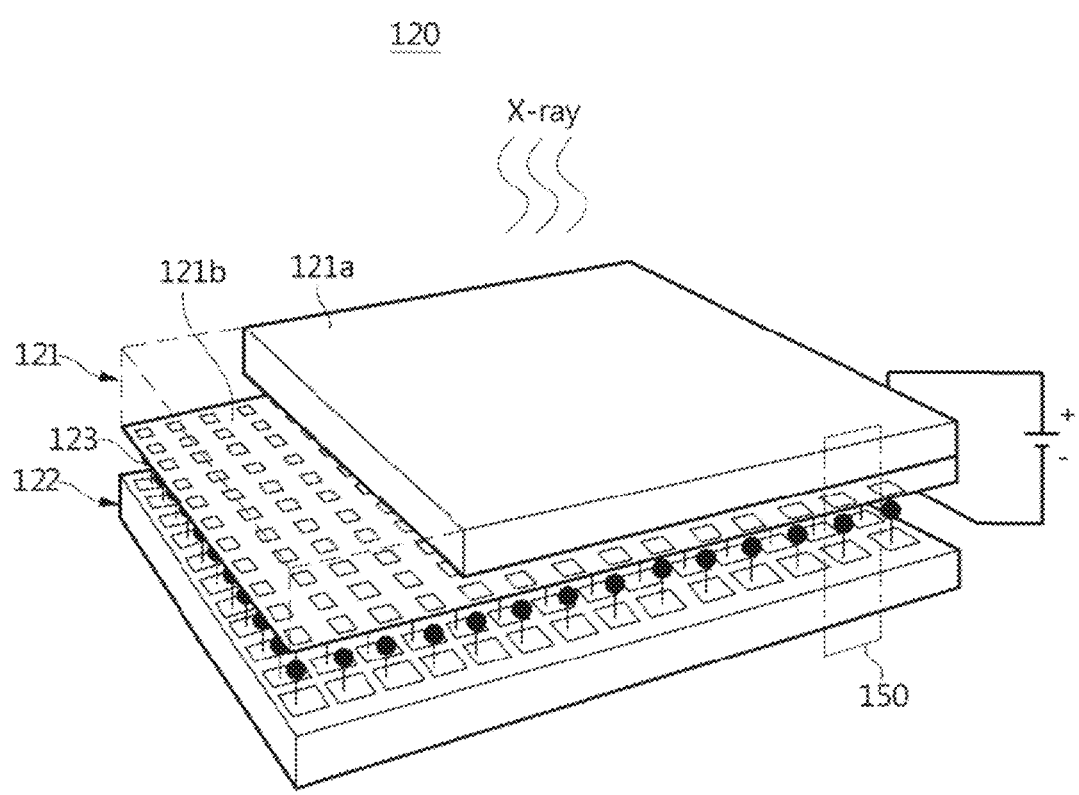
FIG. 7 is a mimetic diagram illustrating a structure of an X-ray detector.

Any method from among the above-described methods may be applied to the X-ray detector 120. In addition, the X-ray detector 120 may have a 2D array structure including a plurality of pixels 150 as shown in FIG. 7. FIG. 7 is a mimetic diagram illustrating a structure of an X-ray detector.

Referring to FIG. 7, the X-ray detector 120 may include a light receiving element 121 that detects X-rays in order to generate electrical signals and a read-out circuit 122 that reads out the generated electrical signals.

As the light receiving element 121, a single crystal semiconductor material may be used in order to ensure a high resolution, a fast response time, and a high dynamic range with low energy and a small dose, and in this instance, any of Ge, CdTe, CdZnTe, GaAs, or the like may be used as the single crystal semiconductor material.

The light receiving element 121 may form a PIN photodiode in which a p-type semiconductor substrate 121c with a 2D array structure is joined in a lower portion of a high-resistance n-type semiconductor substrate 121b.

The read-out circuit 122 using a CMOS process may form a 2D array structure to be coupled with the p-type substrate 121c of the light receiving element 121 for each pixel 150.

In this instance, as the coupling method, a flip-chip bonding method in which a bump 123 such as solder (PbSn), indium (In), or the like is formed and then is compressed by performing reflow on the bump 123 and applying heat to the bump 123 may be used. However, the above-described structure is merely an example, and the structure of the X-ray detector 120 is not limited thereto.

The image processing unit 500 receives first X-ray image data from the X-ray detector 120 or the storage unit 400, and generates at least one X-ray image obtained by performing scatter correction on the first X-ray image data. The image processing unit 500 will be described in more detail with reference to FIGS. 8, 9, 10, 11, and 12.

Figure 8:
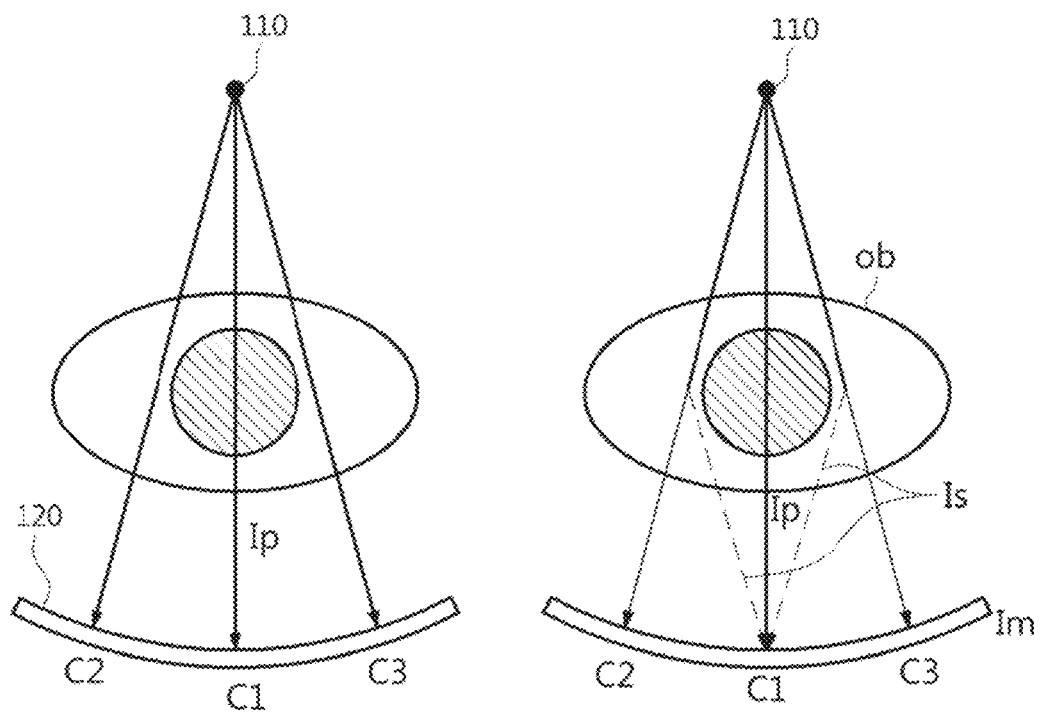
FIG. 8 illustrates a scatter component included in first X-ray image data.
Figure 9:
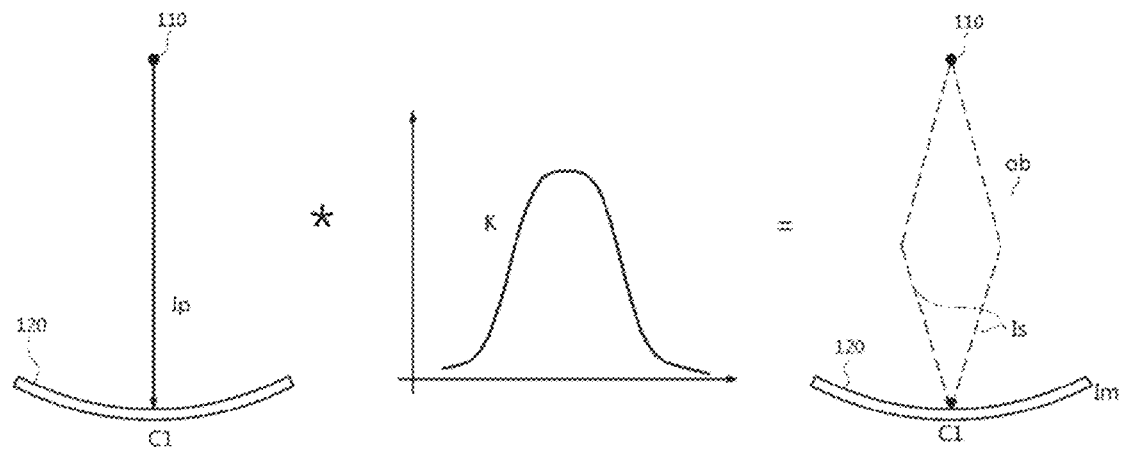
FIG. 9 illustrates a scatter component displayed through a kernel function.

FIG. 8 illustrates a scatter component included in first X-ray image data, and FIG. 9 illustrates a scatter component displayed through a kernel function.

The X-rays radiated from the X-ray source 110 are attenuated in their intensities in accordance with an attenuation coefficient which corresponds to a material constituting the object (ob), a thickness of the object (ob), and the like while propagating through the object (ob). In particular, an attenuation phenomenon of X-rays occurs.

When it is assumed that there is no scattering by the object (ob), a propagation path of the X-rays is not changed or scattering of the X-rays does not occur despite the attenuation phenomenon in which X-rays are attenuated in their intensities while propagating through the object (ob). In this aspect, the X-rays reach the X-ray detector 120 while maintaining a straight line direction. As shown on the left in FIG. 8, the X-rays reaching the X-ray detector 120 may be simply represented as three straight lines, and arrival points of the X-rays on the X-ray detector 120 may be represented as C1, C2, and C3. In this manner, the X-rays that reach the X-ray detector 120 without being scattered by the object (ob), for example, straight line X-rays, may be defined as a primary component. In addition, for convenience of description, the primary component that reaches C1 is hereinafter represented as $I_p$.

However, when the object (ob) is between the X-ray source 110 and the X-ray detector 120, the X-rays radiated from the X-ray source 110 may be scattered in addition to the attenuation phenomenon while propagating through the object (ob), unlike the above-described assumption. In particular, the X-rays radiated from the X-ray source 110 are subjected to a scattering process in which the X-rays collide with the object (ob) to be scattered in various directions, and are added and subtracted with peripheral X-rays while deviating from the straight line direction.

Thus, the X-rays detected at each point of the X-ray detector 120 include a scatter component in addition to the primary component. For example, the X-rays detected at C1 of the X-ray detector 120 include the primary component $I_p$ and X-rays scattered from the peripheral X-rays, that is, the scatter component $I_s$, as shown on the right in FIG. 9. Thus, when the X-rays detected from the X-ray detector 120 or first X-ray image data of the X-ray detector 120 is defined as $I_m$, $I_m$ may be represented as expressed by the following Equation 1.

$$I_m = I_p + I_s \qquad \text{[Equation 1]}$$

Here, $I_m$ denotes first X-ray image data, $I_p$ denotes a primary component, and $I_s$ denotes a scatter component.

Meanwhile, due to the scatter component $I_s$, a data blurring effect may occur in the primary component $I_p$. In particular, as shown in FIG. 9, the scatter component $I_s$ may be acquired by performing a convolution on a predetermined scatter kernel function (hereinafter referred to as "K") that causes data blurring with the primary component $I_p$, and this may be represented as expressed by the following Equation 2.

$$I_s = I_p * K \qquad \text{[Equation 2]}$$

Thus, the image processing unit 500 first acquires the scatter kernel function K which corresponds to the scatter component $I_s$. In addition, the image processing unit 500 performs scatter correction on the first X-ray image data $I_m$ using the scatter kernel function K and a data consistency, and acquires image data that is the same as or close to the primary component $I_p$. In this instance, the image data that is the same as or close to the primary component $I_p$ may be defined as second X-ray image data, and represented as $I_q$. The image processing unit 500 generates an X-ray image based on the second X-ray image data $I_q$. The acquisition of the scatter kernel function, the data consistency, and scatter correction using data consistency will be described in more detail below.

The image processing unit 500 may further perform post-processing on the X-ray image. For example, the image processing unit 500 may correct a brightness and a luminance of a whole or a part of the X-ray image, or correct a contrast or a sharpness thereof. The image post-processing may be performed according to a user's instruction or command or in accordance with a predetermined method.

The image processing unit 500 may transmit the X-ray image or the image obtained by performing post-processing on the X-ray image to the display unit 220, so that a user may determine the transmitted image. In addition, the image processing unit 500 may transmit the X-ray image or the post-processed image to the storage unit 400 so that the storage unit 400 may temporarily or non-temporarily store the transmitted image.

Figure 10:
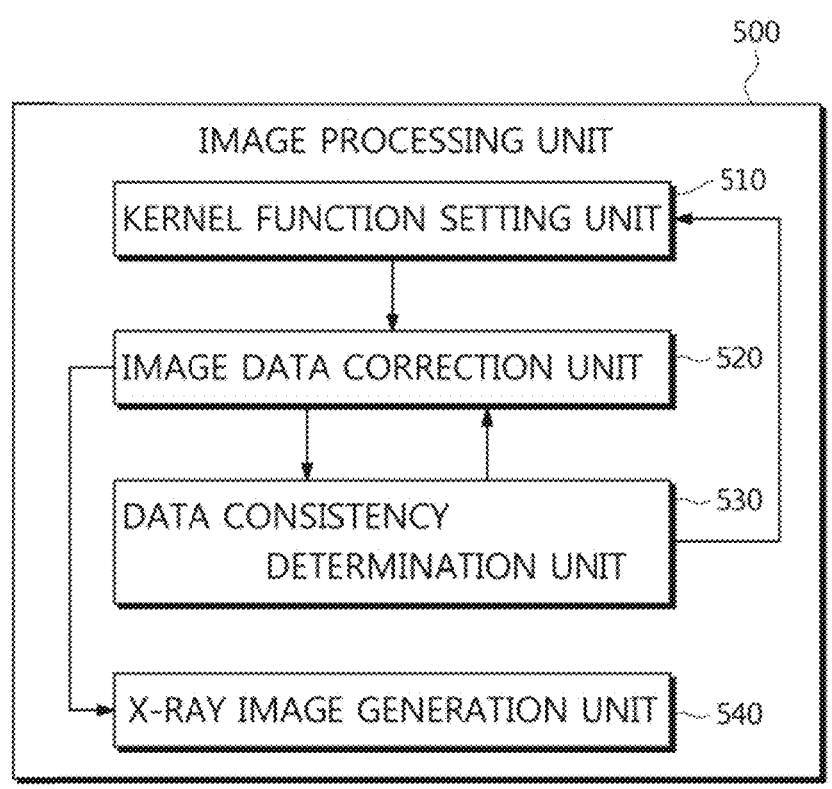
FIG. 10 is a configuration diagram illustrating an image processing unit, in accordance with one exemplary embodiment.

FIG. 10 is a configuration diagram illustrating an image processing unit, in accordance with one exemplary embodiment.

Referring to FIG. 10, the image processing unit 500 may include a kernel function setting unit (also referred to herein as a "kernel function setter") 510, an image data correction unit (also referred to herein as an "image data corrector") 520, a data consistency determination unit (also referred to herein as a "data consistency determiner") 530, and an X-ray image generation unit (also referred to herein as an "X-ray image generator") 540. The kernel function setting unit 510, the image data correction unit 520, the data consistency determination unit 530, and the X-ray image generation unit 540 may be provided in a single processor or a single device, or separately provided in a plurality of processors or a plurality of devices.

The kernel function setting unit 510 sets a scatter kernel function $K_i$ (i=1, 2, 3 . . . , n) in response to the scatter component $I_s$ included in the first X-ray image data. The kernel function setting unit 510 may set an asymmetric kernel function as a scatter kernel function $K_i$. In addition, the kernel function setting unit 510 may update and set the scatter kernel function $K_i$ in order to obtain the scatter kernel function K that satisfies Equation 2, that is, an ideal scatter kernel function K. For example, the kernel function setting unit 510 may set the scatter kernel function at least once such as setting $K_1$ as an initial scatter kernel function, setting $K_2$ obtained by updating $K_1$ as a second scatter kernel function, and setting $K_3$ obtained by updating $K_2$ as a third scatter kernel function. The kernel function setting unit 510 may update the scatter kernel function $K_i$ using the following Equation 3.

$$K_i(I_p, I_0, r) =$$ [Equation 3]

$$A_i \left(\frac{I_p}{i_0}\right)^{\alpha_i} \cdot \left(\ln\left(\frac{I_0}{I_p}\right)\right)^{\beta_i} \cdot \left[\exp\left(\frac{-r^2}{2\sigma_i^2}\right) + B_i\exp\left(\frac{-r^2}{2\tau_i^2}\right)\right],$$

where $i \in N$

Here, N denotes a natural number, each of $A_i$, $B_i$, $\alpha_i$, $\beta_i$, $\sigma_i$, and $\tau_i$ denotes a respective parameter, $I_p$ denotes a primary component included in the first X-ray image data, $I_0$ denotes an X-ray detected without an attenuation phenomenon when there is no object, r denotes a position on an X-ray detector at which each of $I_p$ and $I_0$ is detected, and $K_i(I_p,I_0,r)$ denotes an i-th scatter kernel function.

The kernel function setting unit 510 may apply an approximation of $I_p$ in Equation 3 instead of the primary component $I_p$. In addition, the kernel function setting unit 510 may update the scatter kernel function $K_i$ by updating the 6 parameters ($A_i$, $B_i$, $\alpha_i$, $\beta_i$, $\sigma_i$, $\tau_i$) in Equation 3. Specifically, the kernel function setting unit 510 may define an initial scatter kernel function $K_1$ by setting initial parameters ($A_1$, $B_1$, $\alpha_1$, $\beta_1$, $\sigma_1$, $\tau_1$) and set second parameters ($A_2$, $B_2$, $\alpha_2$, $\beta_2$, $\sigma_2$, $\tau_2$) by updating the initially set parameters, and thereby set a second scatter kernel function $K_2$. In addition, the kernel function setting unit 510 may set third parameters ($A_3$, $B_3$, $\alpha_3$, $\beta_3$, $\sigma_3$, $\tau_3$) by updating the second set parameters, and thereby define a third scatter kernel function $K_3$. In this manner, the kernel function setting unit 510 may update the parameters, and define and update the scatter kernel function $K_i$ using the updated parameters. However, Equation 3 is merely an example of the scatter kernel function, and the scatter kernel function $K_i$ is not limited thereto. In this aspect, the scatter kernel function $K_i$ may be set in any of various forms.

The initial scatter kernel function $K_1$ may be set in accordance with a user's instruction or command, or automatically set by a system. In addition, the kernel function setting unit 510 may update the scatter kernel function until image data that is subjected to scatter correction by the scatter kernel function satisfies data consistency. In this instance, the image data that is subjected to scatter correction may be hereinafter defined as corrected image data $I_{qi}$ (i=1, 2, 3 . . . , n), and the corrected image data satisfying a data consistency or finally generated corrected image data $I_{qi}$ may form second X-ray image data Iq.

In addition, the kernel function setting unit 510 may update the scatter kernel function by using any of manual iteration, an optimization algorithm, for example, a genetic algorithm, or an algorithm such as ant colony optimization or particle swarm optimization. The manual iteration or the optimization algorithm is well known in the art, and thus detailed description thereof will be omitted.

The image data correction unit 520 performs scatter correction on the first X-ray image data $I_m$ by using the scatter kernel function $K_i$ (i=1, 2, 3 . . . , n) set in the kernel function setting unit 510, and generates corrected image data $I_{qi}$ (i=1, 2, 3 . . . , n) and the second X-ray image data $I_q$. The corrected image data $I_{qi}$ (i=1, 2, 3 . . . , n) and the second X-ray image data $I_q$ may be temporarily or non-temporarily stored in the storage unit 400.

The image data correction unit 520 may generate the corrected image data $I_{qi}$ by performing a deconvolution of the first X-ray image data $I_m$ and the scatter kernel function $K_i$ based on Equation 2. For example, the image data correction unit 520 may acquire the corrected image data via a deconvolution method as expressed in the following Equation 4.

$$I_{qi} = F^{-1}\left(\frac{F(I_m)}{F(\delta + K_i)}\right)$$ [Equation 4]

Here, $I_m$ denotes first X-ray image data, $\delta$ denotes a delta function, $K_i$ denotes a scatter kernel function, F denotes a Fourier transform, and $F^{-1}$ denotes an inverse Fourier transform.

However, Equation 4 is merely an example of the deconvolution method, and thus the image data correction unit 520 may use other deconvolution methods without being limited thereto.

When the scatter kernel function $K_i$ is updated by the kernel function setting unit 510, the image data correction unit 520 may sequentially generate the corrected image data $I_{qi}$ with respect to the initially set scatter kernel function and the updated scatter kernel function.

Specifically, when the kernel function setting unit 510 sets $K_1$ as an initial scatter kernel function, the image data correction unit 520 generates first corrected image data $I_{q1}$ by performing a deconvolution on the first X-ray image data $I_m$ and $K_1$, and when the kernel function setting unit 510 sets $K_2$ obtained by updating $K_1$ as a second scatter kernel function, the image data correction unit 520 generates second corrected image data $I_{q2}$ by performing a deconvolution on the first X-ray image data $I_m$ and $K_2$. In addition, when the kernel function setting unit 510 sets $K_3$ obtained by updating $K_2$ as a third scatter kernel function, the image data correction unit 520 generates third corrected image data $I_{q3}$ by performing a deconvolution on the first X-ray image data $I_m$ and $K_3$. In this manner, the corrected image data $I_{qi}$ may be sequentially generated with respect to all of the scatter kernel function $K_i$ generated in the kernel function setting unit 510 according to the generation order of the scatter kernel function $K_i$.

The image data correction unit 520 may acquire the finally generated corrected image data as second X-ray image data $I_q$.

The data consistency determination unit 530 may determine whether the corrected image data $I_{qi}$ generated in the image data correction unit 520 satisfies a data consistency. When a plurality of pieces of corrected image data are generated, the data consistency determination unit 530 determines whether each piece of corrected image data satisfies the data consistency. Data consistency will be described in detail with reference to FIG. 11.

Figure 11:
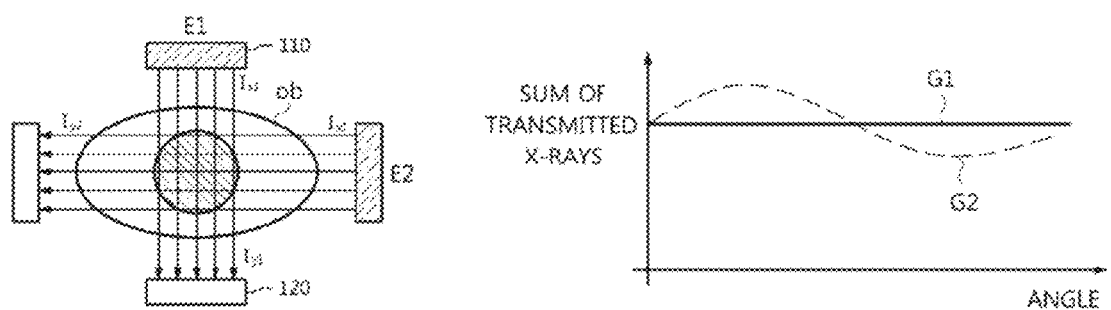
FIG. 11 illustrates data consistency.

FIG. 11 illustrates data consistency.

Data consistency is one characteristic of the Radon transform that is a basic principle of computer tomography, and means that a sum of attenuation coefficients of X-rays with respect to parallel beams or a sum of transmitted X-rays detected from the X-ray detector 120 with respect to parallel beams is constant regardless of an angle of the radiography.

On the left side of FIG. 11, the X-ray source 110 that radiates X-rays of parallel beams in directions E1 and E2 is shown. In this instance, the X-rays radiated in the direction E1 may be defined as $I_{x1}$, and the X-rays radiated in the direction E2 may be defined as $I_{x2}$. In response to this, transmitted X-rays which are detected by the X-ray detector 120 in the direction E1 may be defined as $I_{y1}$, and transmitted X-rays which are detected by the X-ray detector 120 in the direction E2 may be defined as $I_{y2}$.

The intensity of the X-rays may be the same or different in accordance with a radiation position of the parallel beam. Similarly, the intensity of the X-rays $I_{x2}$ may be the same or different in accordance with the radiation position of the parallel beam. In addition, the strength of the transmitted X-rays $I_{y1}$ may be the same or different in accordance with a detection position, and the transmitted X-rays $I_{y2}$ may be the same or different in accordance with the detection position.

As described above, the attenuation phenomenon in which the X-rays are attenuated in their intensities while propagating through the object (ob) may occur, and in this instance, the attenuation coefficient may be represented as $$\ln\left(\frac{I_{x1}}{I_{y1}}\right), \ln\left(\frac{I_{x2}}{I_{y2}}\right)$$

with respect to each direction, that is, the directions E1 and E2 respectively.

According to data consistency, a sum of the attenuation coefficients $$\ln\left(\frac{I_{x1}}{I_{y1}}\right)$$

in the direction E1 may be the same as a sum of the attenuation coefficients $$\ln\left(\frac{I_{x2}}{I_{y2}}\right)$$

in the direction E2. In addition, when the same X-rays are radiated in the directions E1 and E2, a sum of the transmitted X-rays $I_{y1}$ detected in the direction E1 may be the same as a sum of the transmitted X-rays $I_{y2}$ detected in the direction E2. Thus, the relationship between the angle of radiography and the sum of the transmitted X-rays may have a form of a constant function, like a graph G1 shown on the right side of FIG. 11. However, when the data consistency is inhibited due to the scattering phenomenon of the X-rays, the relationship between the angle of radiography and the sum of the transmitted X-rays deviates from the form of the constant function, as shown in a graph G2. In contrast, scatter correction may mean that change is applied to the transmitted X-rays so that the relationship between the angle of radiography and the sum of the transmitted X-rays has the form of the constant function, that is, satisfies the data consistency.

The data consistency determination unit 530 assumes that the corrected image data $I_{qi}$ generated in the image data correction unit 530 is based on transmitted X-rays, and determines whether the corrected image data satisfies the data consistency based on this. The data consistency determination unit 530 may determine suitability of the scatter kernel function $K_i$ or the degree of scatter correction by determining whether the corrected image data satisfies the data consistency. When a plurality of pieces of corrected image data are generated in the image data correction unit 530, the data consistency determination unit 530 sequentially determines whether the corrected image data satisfies the data consistency in accordance with the generation order of the corrected image data.

When the corrected image data $I_{qi}$ does not satisfy the data consistency, the scatter kernel function $K_i$ may be updated by the kernel function setting unit 510, and therefore the corrected image data may be re-generated in the image data correction unit 520.

For example, when the data consistency determination unit 530 determines that first corrected image data $I_{q1}$ does not satisfy the data consistency, the kernel function setting unit 510 sets an updated scatter kernel function $K_2$, and the image data correction unit 520 generates second corrected image data $I_{q2}$ based on $K_2$. The data consistency determination unit 530 re-determines whether the second corrected image data $Iq_2$ satisfies the data consistency. When the second corrected image data $Iq_2$ is determined not to satisfy data consistency by the data consistency determination unit 530, the kernel function setting unit 510 sets an updated scatter kernel function $K_3$, and the image data correction unit 520 generates third corrected image data $I_{q3}$ based on $K_3$. In this manner, based on the determination of the data consistency determination unit 530, the scatter kernel function $K_i$ and the corrected image data may be updated.

Conversely, when the corrected image data $I_{qi}$ satisfies the data consistency, the image data correction unit 520 or the data consistency determination unit 530 may use this as second X-ray image data $I_q$, and transmit the second X-ray image data $Iq$ to the X-ray image generation unit 540.

As described above, the data consistency is established for the parallel beam, and therefore, when the X-ray source 110 radiates fan beam X-rays, the data consistency determination unit 530 may perform conversion of image data according to a beam type prior to determination of the data consistency. In this instance, corrected image data generated by radiating the fan beam may be referred to as fan beam corrected image data, and corrected image data generated by radiating the parallel beam may be referred to as parallel beam corrected image data.

Figure 12:
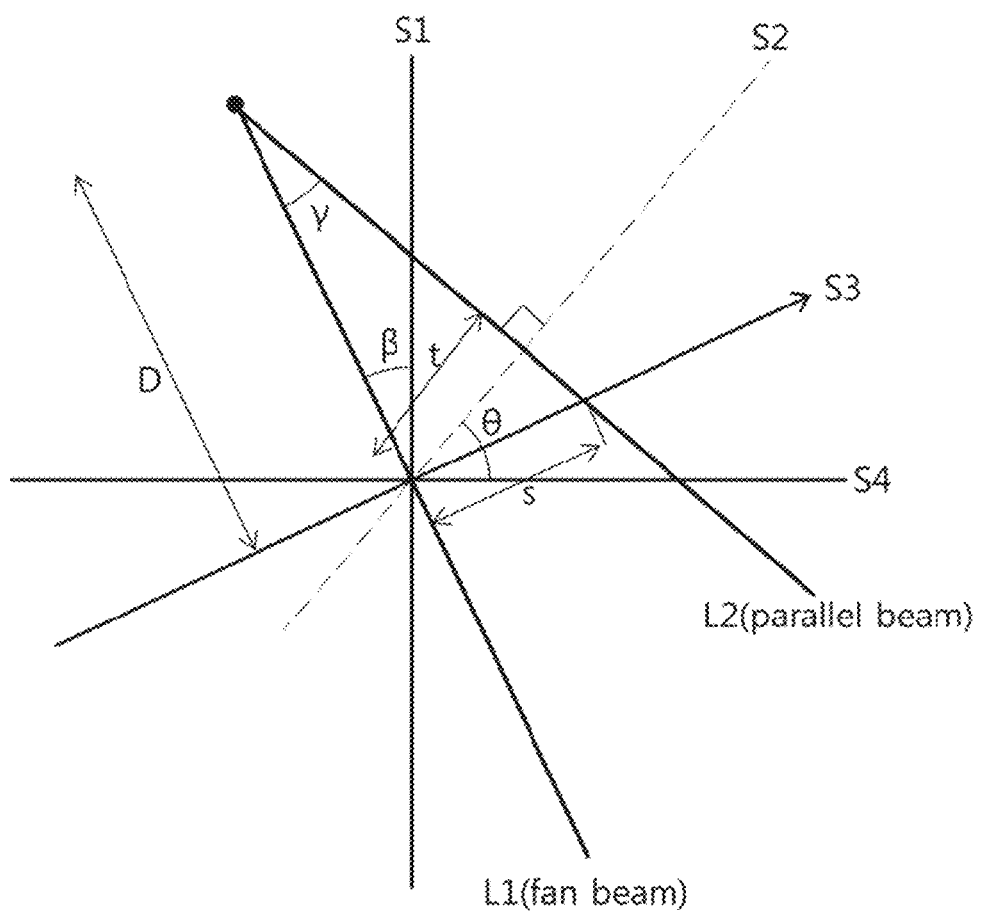
FIG. 12 illustrates conversion of image data according to a beam type.

FIG. 12 illustrates conversion of image data according to a beam type.

As shown in FIG. 12, when it is assumed that L1 is a fan beam and L2 is a parallel beam, a fan angle may be defined as an angle γ formed by L1 and L2, a fan beam angle may be defined as an angle β formed by a reference line S1 and L1, and a parallel beam angle may be defined as an angle θ formed by a reference line S2 and L2. In addition, when a distance between L1 and L2 on the reference line S2 is defined as t, a distance between L1 and L2 on a reference line S4 is defined as s, and a radiation distance of the X-rays up to a reference line S3 is defined as D, θ and t may be represented as expressed by the following Equations 5.

$$\theta = \beta + \gamma = \beta + \tan^{-1}\left(\frac{s}{D}\right) \qquad \text{[Equations 5]}$$

$$t = s \cdot \cos\gamma = \frac{sD}{\sqrt{D^2 + s^2}}$$

The data consistency determination unit 530 may perform fan-parallel rebinning in which fan beam corrected image data is converted with respect to θ and t using Equations 5, that is, the fan beam corrected image data is converted into parallel beam corrected image data.

When fan-parallel rebinning is performed on the corrected image data $I_{qi}$, the data consistency determination unit 530 determines whether corrected image data obtained after the conversion satisfies the data consistency. The data consistency determination unit 530 may determine whether the corrected image data generated in at least two directions satisfies the data consistency.

As described above, the X-ray source 110 radiates X-rays multiple times at a predetermined time interval while the gantry 102 is rotated. In particular, the X-ray source 110 radiates the X-rays in each of a plurality of directions, and accordingly, the image data correction unit 520 generates the corrected image data $Iq_i$ in each of the plurality of directions. The data consistency determination unit 530 compares the corrected image data in at least two directions among a plurality of pieces of the generated corrected image data, and determines a data consistency condition. For example, the data consistency determination unit 530 may compare corrected image data (hereinafter referred to as $I_{qi\_1}$) generated in a direction P11 of FIG. 2 and corrected image data (hereinafter referred to as $I_{qi\_2}$) generated in a direction P21 to determine the data consistency condition.

The data consistency determination unit 530 may determine whether a difference of the sum of attenuation coefficients or a difference of the sum of the transmitted X-rays is smaller than a predetermined value $\epsilon$ based on the corrected image data in at least two directions, thereby determining whether the corrected image data satisfies the data consistency. In this instance, the difference of the sum of attenuation coefficients or the difference of the sum of the transmitted X-rays may be calculated as L1-norm or L2-norm, but is not limited thereto. In addition, $\epsilon$ may be defined in advance by a user or determined in accordance with setting of a system.

As in the above-described example, the data consistency determination unit 530 may calculate a sum A1 of attenuation coefficients from the corrected image data $I_{qi\_1}$ in the direction P11, calculate a sum A2 of attenuation coefficients from the corrected image data $I_{qi\_2}$ in the direction P21, and determine whether the corrected image data satisfies the data consistency only when a difference of A1 and A2 is smaller than $\epsilon$. The data consistency determination unit 530 may calculate a sum B1 of transmitted X-rays in the direction P11 (that is, a sum of corrected image data $I_{qi\_1}$), calculate a sum B2 of transmitted X-rays in the direction P21 (that is, a sum of corrected image data $I_{qi\_2}$), and determine that the corrected image data satisfies the data consistency only when a difference of B1 and B2 is smaller than $\epsilon$.

The X-ray image generation unit 540 may receive the corrected image data $I_{qi}$ satisfying the data consistency, that is, second X-ray image data $I_q$, from the image data correction unit 520 or the data consistency determination unit 530, and generate an X-ray image which corresponds to the second X-ray image data $I_q$. The X-ray image generation unit 540 may further perform post-processing on the X-ray image.

The X-ray image generated in the X-ray image generation unit 540 or an image obtained by performing post-processing on the X-ray image may be displayed via the display unit 220.

The storage unit 400 stores data and programs for operations of the X-ray imaging apparatus 1.

As an example of data storage, the storage unit 400 may store any one or more of a rotation rate or rotation speed of the gantry 102, the number of radiations of the X-ray source 110, the dose of the radiated X-rays and the like when radiography is performed. The storage unit 400 may store any one or more of the first X-ray image data $I_m$ acquired from the X-ray detector 120, the scatter kernel function $K_i$ set in the image processing unit 500, the corrected image data $I_{qi}$ or the second X-ray image data $I_q$ generated from the image processing unit 500, and the like.

As an example of program storage, the storage unit 400 may store any one or more of a program for setting the scatter kernel function $K_i$, a program for generating the corrected image data $I_{qi}$, a program for determining data consistency, and the like.

Such a storage unit 400 may include a storage medium of at least one type from among a flash memory, a hard disk, a multimedia card micro type, a card memory (for example, an SD or XD memory, etc.), a random access memory (RAM), a static RAM (SRAM), a read-only memory (ROM), an electrically erasable programmable ROM (EEPROM), a programmable ROM (PROM), a magnetic memory, a magnetic disk, and an optical disc. However, the storage unit 400 is not limited thereto, and may be implemented in other arbitrary forms which are well known in the art. In addition, a consumer electronic apparatus 100 may operate a web storage that performs a storage function on the Internet.

The control unit 300 may control overall operations of the X-ray imaging apparatus 1 by generating a predetermined control command and transmitting the generated control command to any one or more of the X-ray source 110, the X-ray detector 120, the storage unit 400, the image processing unit 500, and the like. The control unit 300 may control the operations of the X-ray imaging apparatus 1 in accordance with a user's instruction or command input from the input unit 210, or in accordance with a predetermined setting.

For example, the control unit 300 may control a rotation of the gantry 102 and a rotation of the X-ray source 110 and the X-ray detector 120. The control unit 300 may generate control signals and transmit the generated control signals to the X-ray source 110 so that the X-ray source 110 applies power of a predetermined voltage to the X-ray tube 111 to generate X-rays with predetermined energy. In addition, the control unit 300 may control various operations of the X-ray detector 120, such as, for example, a read-out operation of the X-rays. The control unit 300 may control the first X-ray image data $I_m$ of the X-ray detector 120 to be transmitted to the storage unit 400, and/or control the storage unit 400 to temporarily or non-temporarily store the first X-ray image data $I_m$.

The control unit 300 may transmit any of a variety of control signals for generation of the X-ray image to the image processing unit 500. For example, the control unit 300 may control the image processing unit 500 to generate the scatter kernel function $K_i$ by using Equation 3 and to generate the corrected image data $I_{qi}$ and the second X-ray image data $I_q$ by using Equation 4. The control unit 300 may control the image processing unit 500 to perform fan-parallel rebinning by using Equations 5 so that it is determined whether the corrected image data $I_{qi}$ satisfies a data consistency. The control signals may be generated so that the X-ray image may be displayed via the display unit 220.

The control unit 300 may be implemented as any one or more of a variety of processors including at least one chip in which an integrated circuit is formed. Such a central processing unit (CPU) may be provided in a single process or a single device, or may be separately provided in a plurality of processors or a plurality of devices.

Figure 13:
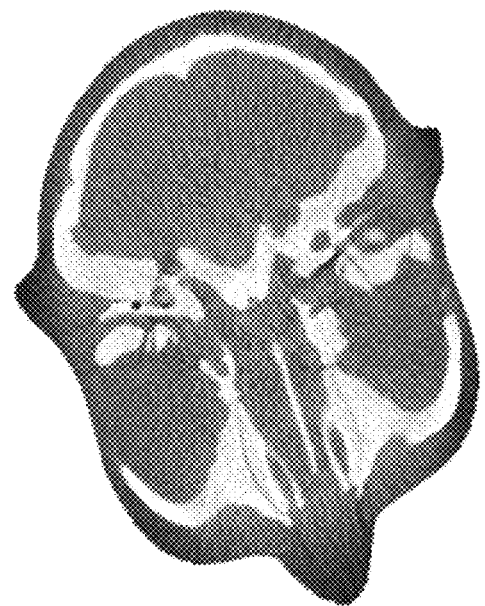
FIG. 13 illustrates an X-ray image generated by an X-ray imaging apparatus.
Figure 13:
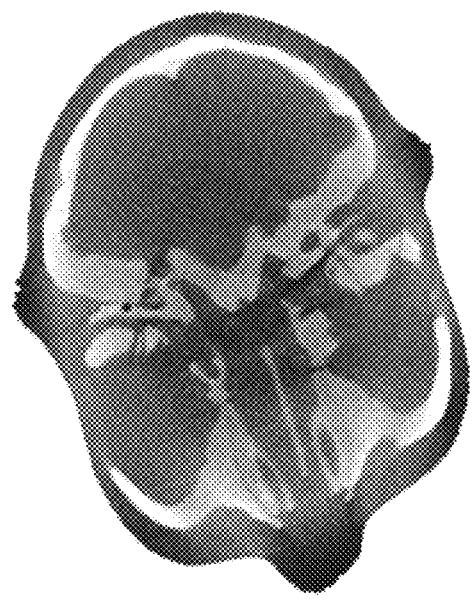

FIG. 13 illustrates an X-ray image generated by an X-ray imaging apparatus.

In FIG. 13, an image (a) shows image data before performing scatter correction, that is, an X-ray image generated to correspond to the first X-ray image data $I_m$, and an image (b) shows image data after performing scatter correction using the scatter kernel function $K_i$ and the data consistency, that is, an X-ray image generated to correspond to the second X-ray image data $I_q$.

In the image (a) of FIG. 13, a phenomenon in which the boundaries of the whole or partial region are unclear or blurred due to the scatter component occurs. Conversely, as shown in the image (b) of FIG. 13, it can be seen that the boundaries between tissues are clearly shown in the X-ray image on which scatter correction has been performed and a uniform resolution is maintained in all regions.

The X-ray imaging apparatus that performs scatter correction by using the scatter kernel function Ki and a data consistency has been described above based on the control block diagram, and a control method for the X-ray imaging apparatus will be described with reference to FIG. 14.

Figure 14:
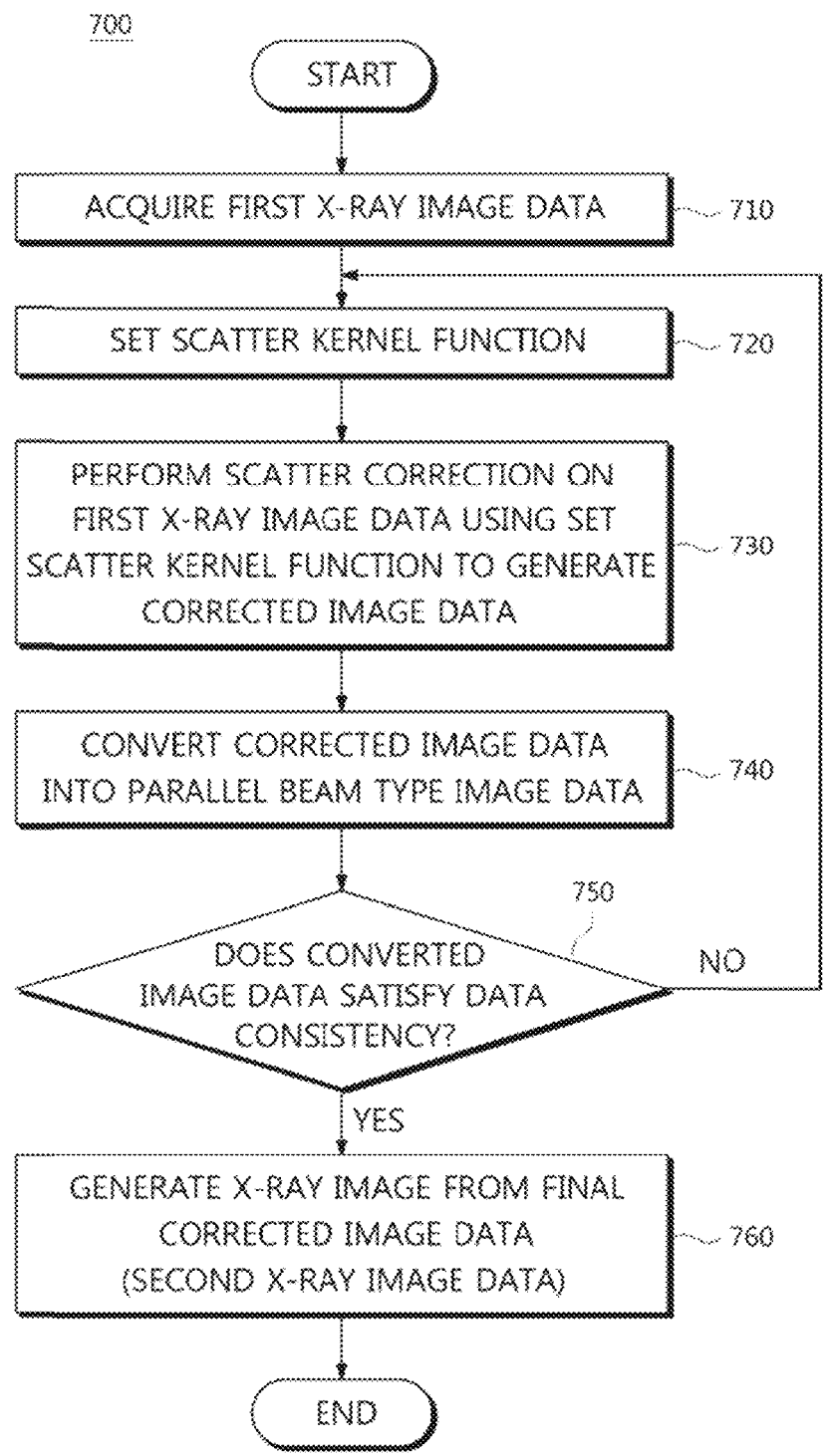
FIG. 14 is a flowchart illustrating a control method for an X-ray imaging apparatus, in accordance with one exemplary embodiment.

FIG. 14 is a flowchart illustrating a control method for an X-ray imaging apparatus, in accordance with one exemplary embodiment of the present invention.

Referring to flowchart 700 of FIG. 14, in operation 710, the X-ray imaging apparatus 1 first acquires first X-ray image data $I_m$.

Specifically, the X-ray source 110 radiates X-rays multiple times while rotating in a direction D1 along with the rotation of the gantry 102. The X-ray detector 120, which is positioned to face the X-ray source 110, detects X-rays which have propagated through an object (ob) in response to each instance of radiation of X-rays, and acquires the first X-ray image data $I_m$.

Next, in operation 720, the X-ray imaging apparatus 1 sets the scatter kernel function $K_i$.

The image processing unit 500 may set a kernel function that satisfies Equation 2, that is, a kernel function that is the same as or close to an ideal scatter kernel function K, as the scatter kernel function $K_i$. The image processing unit 500 may update and set the scatter kernel function $K_i$ so as to be closer to K, and in this instance, an initial scatter kernel function, that is, $K_1$, may be set in accordance with a user's instruction or command or automatically set by a system. In addition, the scatter kernel function $K_i$ may be updated by using Equation 3.

In operation 730, the image processing unit 500 performs scatter correction on the first X-ray image data $I_m$ by using the set scatter kernel function $K_i$, and generates corrected image data $I_{qi}$.

The image processing unit 500 may generate the corrected image data $I_{qi}$ by performing a deconvolution of the first X-ray image data $I_m$ and the scatter kernel function $K_i$ based on Equation 2. The image processing unit 500 may acquire the corrected image data $I_{qi}$ by using the deconvolution method shown in Equation 4.

When the scatter kernel function $K_i$ is updated, the image processing unit 500 generates the corrected image data $I_{qi}$ using the updated scatter kernel function $K_i$.

In operation 740, the image processing unit 500 converts the corrected image data $I_{qi}$ into parallel beam corrected image data.

The image processing unit 500 performs fan-parallel rebinning in which the fan beam corrected image data is converted with respect to θ and t by using Equations 5 to thereby acquire the converted corrected image data.

However, when parallel beam X-rays are radiated from the X-ray source 110 and the corrected image data $I_{qi}$ is generated based on the radiated parallel beam X-rays, operation 740 may be omitted.

In operation 750, the image processing unit 500 determines whether the corrected image data obtained after the conversion satisfies a data consistency condition when fan-parallel rebinning is performed on the corrected image data $I_{qi}$. The image processing unit 500 may determine whether the corrected image data (or converted corrected image data) generated in at least two directions along with the rotation of the gantry 102 satisfies the data consistency.

When the corrected image data does not satisfy the data consistency, the image processing unit 500 returns to operation 720 in order to update the scatter kernel function $K_i$.

Conversely, in operation 760, when the corrected image data satisfies the data consistency, the image processing unit 500 generates an X-ray image which corresponds to the second X-ray image data $I_q$ by using the corrected image data which satisfies the data consistency or by using finally generated corrected image data as the second X-ray image data $I_q$.

The control method for the X-ray imaging apparatus may further include performing post-processing. The X-ray image generated in this manner or the image obtained by performing post-processing on the X-ray image may be displayed via the display unit 220.

According to the X-ray imaging apparatus and the control method for the same, scatter correction is performed by using a data consistency so that accuracy of the scatter correction may be increased and an X-ray image may be generated based on the accuracy, thereby improving quality of the X-ray image.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:

1. An X-ray imaging apparatus comprising:
a processor configured to set a scatter kernel function in response to a scatter component included in first X-ray image data detected by an X-ray detector and generate second X-ray image data obtained by performing scatter correction on the first X-ray image data by using the scatter kernel function and a data consistency; and
a display configured to display an X-ray image reconstructed from the second X-ray image data,
wherein the processor is further configured to generate corrected image data obtained by performing scatter correction on the first X-ray image data by using the scatter kernel function, determine whether a parallel-beam type corrected image converted from the corrected image data by performing fan-parallel rebinning satisfies the data consistency and determine whether to update the scatter kernel function based on a data consistency of the parallel-beam type corrected image data.

2. The X-ray imaging apparatus according to claim 1, wherein the processor is further configured to generate the corrected image data by performing a deconvolution on the first X-ray image data and the scatter kernel function.

3. The X-ray imaging apparatus according to claim 2, wherein the processor is further configured to perform the deconvolution on the first X-ray image data and the scatter kernel function by using the following Equation 4:

$$I_{qi} = F^{-1}\left(\frac{F(I_m)}{F(\delta + K_i)}\right) \quad \text{[Equation 4]}$$

where $I_{qi}$ denotes corrected image data, $I_m$ denotes first X-ray image data, $\delta$ denotes a delta function, $K_i$ denotes a scatter kernel function, F denotes a Fourier transform, and $F^{-1}$ denotes an inverse Fourier transform.

4. The X-ray imaging apparatus according to claim 1, wherein the second X-ray image data satisfies the data consistency.

5. The X-ray imaging apparatus according to claim 1, wherein the processor is further configured to update the scatter kernel function when the corrected image data is determined as not satisfying the data consistency.

6. The X-ray imaging apparatus according to claim 5, wherein the processor is further configured to set or update the scatter kernel function using the following Equation 3:

$$K_i(I_p, I_0, r) = A_i \left(\frac{I_p}{i_0}\right)^{\alpha_i} \cdot \left(\ln\left(\frac{I_0}{I_p}\right)\right)^{\beta_i} \cdot \left[\exp\left(\frac{-r^2}{2\sigma_i^2}\right) + B_i \exp\left(\frac{-r^2}{2\tau_i^2}\right)\right],$$ [Equation 3]

where $i \in N$, N denotes a natural number, each of $A_i$, $B_i$, $\alpha_i$, $\beta_i$, $\sigma_i$, and $\tau_i$ denotes a respective parameter, $I_p$ denotes a primary component included in the first X-ray image data, $I_0$ denotes an X-ray detected without an attenuation phenomenon when there is no object, r denotes a position on an X-ray detector at which each of $I_p$ and $I_0$ is detected, and $K_i(I_p,I_0,r)$ denotes an i-th scatter kernel function.

7. A control method which is executable by an X-ray imaging apparatus, the control method comprising:
  setting a scatter kernel function in response to a scatter component included in first X-ray image data detected by an X-ray detector; and
  generating second X-ray image data obtained by performing scatter correction on the first X-ray image data by using the scatter kernel function and a data consistency,
  wherein the generating the second X-ray image data includes generating corrected image data obtained by performing scatter correction on the first X-ray image data by using the scatter kernel function;
  determining whether a parallel-beam type corrected image converted from the corrected image data by performing fan-parallel rebinning satisfies the data consistency; and
  determining whether to update the scatter kernel function based on a data consistency of the parallel-beam type corrected image data.

8. The control method according to claim 7, wherein the generating the second X-ray image data includes generating the corrected image data by performing a deconvolution on the first X-ray image data and the scatter kernel function.

9. The control method according to claim 8, wherein the generating the second X-ray image data includes performing the deconvolution on the first X-ray image data and the scatter kernel function using the following Equation 4:

$$I_{qi} = F^{-1}\left(\frac{F(I_m)}{F(\delta + K_i)}\right)$$ [Equation 4]

where $I_{qi}$, denotes corrected image data, $I_m$ denotes first X-ray image data, $\delta$ denotes a delta function, $K_i$ denotes a scatter kernel function, F denotes a Fourier transform, and $F^{-1}$ denotes an inverse Fourier transform.

10. The control method according to claim 7, wherein the second X-ray image data satisfies the data consistency.

11. The control method according to claim 7, wherein the setting the scatter kernel function includes updating the scatter kernel function when the corrected image data is determined as not satisfying the data consistency.

12. The control method according to claim 11, wherein the setting the scatter kernel function includes setting or updating the scatter kernel function using the following Equation 3:

$$K_i(I_p, I_0, r) = A_i \left(\frac{I_p}{i_0}\right)^{\alpha_i} \cdot \left(\ln\left(\frac{I_0}{I_p}\right)\right)^{\beta_i} \cdot \left[\exp\left(\frac{-r^2}{2\sigma_i^2}\right) + B_i \exp\left(\frac{-r^2}{2\tau_i^2}\right)\right]$$ [Equation 3]

where $i \in N$, N denotes a natural number, each of $A_i$, $B_i$, $\alpha_i$, $\beta_i$, $\sigma_i$, and $\tau_i$ denotes a respective parameter, $I_p$ denotes a primary component included in the first X-ray image data, $I_0$ denotes an X-ray detected without an attenuation phenomenon when there is no object, r denotes a position on an X-ray detector at which each of $I_p$ and $I_0$ is detected, and $K_i(I_p,I_0,r)$ denotes an i-th scatter kernel function.

13. The control method according to claim 7, further comprising displaying an X-ray image reconstructed from the second X-ray image data.

* * * * *